(12) United States Patent
Jones (10) Patent No.: US 7,674,223 B2
(45) Date of Patent: Mar. 9, 2010

(54) DOOR LATCHING MECHANISM FOR INFANT CARE APPARATUS

(75) Inventor: Thomas C. Jones, Columbia, MD (US)

(73) Assignee: General Electric Company, Schenectady, NY (US)

( * ) Notice: Subject to any disclaimer, the term of this patent is extended or adjusted under 35 U.S.C. 154(b) by 1371 days.

(21) Appl. No.: 11/098,930

(22) Filed: Apr. 5, 2005

(65) Prior Publication Data

US 2006/0218727 A1    Oct. 5, 2006

(51) Int. Cl.
*A61G 11/00*    (2006.01)
(52) U.S. Cl. ............................................. 600/22; 5/655
(58) Field of Classification Search ............. 600/21–22; 49/145–147, 157, 197, 211, 364, 142, 159, 49/163, 190, 262, 394; 220/326; 5/93.1, 5/97, 655; 292/340, 341.15, 341.17
See application file for complete search history.

(56) References Cited

U.S. PATENT DOCUMENTS 5,016,926 A * 5/1991 Sharp et al. .................... 292/42
5,129,879 A * 7/1992 Mattson ........................ 600/22
5,174,618 A * 12/1992 Kropf .......................... 292/254
6,569,080 B2 * 5/2003 Dykes et al. .................. 600/22
6,929,597 B2 * 8/2005 Hampe ........................ 600/22

* cited by examiner

*Primary Examiner*—Charles A Marmor, II
*Assistant Examiner*—Carrie Harris
(74) *Attorney, Agent, or Firm*—Roger M. Rathbun (57) ABSTRACT

An infant care apparatus having a door latching mechanism that provides a positive latching of a door to the hood of the apparatus. The mechanism has a door latching assembly that is affixed to the door and which is latched to a floating catch housing that is affixed to the hood in a manner that the floating catch housing is vertically movable with respect to the hood. When the door is moved into its closed, latched position, the door latching assembly vertically aligns the floating catch housing so that a movable latch member is correctly oriented with respect to latch openings in the floating catch housing so that the movable catch member can enter the latch openings sufficiently to assure a positive, secure latch therebetween.

19 Claims, 5 Drawing Sheets

DOOR LATCHING MECHANISM FOR INFANT CARE APPARATUS

BACKGROUND

The present invention relates to an infant care apparatus and, more particularly, to an improved door latching mechanism for the doors of an infant incubator.

In the normal infant incubator, the construction generally includes an infant compartment within which the infant is positioned and which provides the infant with a controlled environment to aid in the well-being of the infant. That infant compartment must, of course, provide ready access to the infant to carry out various interventions that may be desired to assist the infant or to place the infant within the infant compartment or to remove the infant therefrom.

Accordingly, it is common for an infant incubator to have side walls and end walls surrounding the infant as well as a hood overhead of the infant in the formation of the infant compartment and also to include doors that can be opened and closed for the aforedescribed access to the infant contained within that infant compartment. The doors may also be of differing designs and constructions and may be a single door spanning between end walls as shown and described in U.S. Pat. No. 6,569,080 of Dykes et al where the single side door is pivoted along a horizontal axis or, alternatively, there may be two doors in the form of "barn doors" that are pivoted along vertical axes at the external edges of the doors and which doors come together at about the middle of the incubator side when the doors are closed and the internal edges abut against each other or slightly overlap each other.

No matter the particular design of the doors as described, there is a need for a latching mechanism to allow the door or doors to be freely opened and closed where the doors must be positively and securely latched in the closed position to ensure the safety of the infant enclosed in the infant compartment. Thus, the free or non-pivoted internal edges must be securely latched to the hood in a positive manner that assures the caregiver of the integrity that the door is closed and will remain closed until deliberately unlatched by the caregiver in gaining access to the interior of the infant compartment.

One convenient latch for such purposes is that shown and described in the aforementioned U.S. Pat. No. 6,569,080 of Dykes et al where a vertically movable latch member is biased upwardly to engage into a recess affixed to the hood. While perfectly acceptable for the hood arrangement described in that patent, there are instances of other types of incubators where the use of a vertically movable latch member has some deficiencies.

For example, there are incubators that are designed to operate in a high humidity atmosphere within the infant compartment for lengthy periods of time, that is, for days or even weeks at a time. The presence of high humidity causes warpage of certain plastic materials used in incubators and that warpage moves the plastic materiel away from the area of high humidity in the direction toward the low humidity atmosphere. Accordingly, with certain incubators, the warpage moves the hood as well as doors outwardly with respect to the infant compartment, and if the movement is too extreme, the vertically movable latch member of the '080 patent will not engage the hood sufficiently and there is a problem that the caregiver will not be able to fully secure the door to the hood. As an example, the edge of an infant care apparatus hood may warp on the order of 0.2 to 0.3 inches over the course of two to four weeks of high humidity and therefore can raise real problems in the integrity of a latching mechanism used to latch a door to a hood.

The problem is even more pronounced where there are two doors, that is, the barn door design, along the side of the incubator and where those doors are pivotable along a vertical axis located at the outer edges of the doors such that the latching mechanism must allow the individual latching and unlatching of the inner abutting edges of the doors to the overhead hood while taking into account the possibility of warpage of either or both doors as well as the hood itself.

Accordingly, it would be advantageous to have an infant apparatus that includes a latching mechanism that ensures the positive latching between the door or doors of the apparatus even where there is warpage of the plastic material used in constructing the hood and the doors.

SUMMARY OF THE INVENTION

Accordingly, the present invention relates to an infant care apparatus having a latching means that provides a secure, positive latching of a door to the hood of the apparatus even when there has been warpage of the door and/or the hood.

Thus the infant care apparatus has a base that underlies an infant support on which an infant is adapted to lie while being treated by the apparatus. The apparatus also has end and side walls that extend upwardly from the base and a hood that is located atop of those walls to form an infant compartment therein where the environment is controlled for the infant by providing control of the heat and humidity within that infant compartment.

One of the side walls is comprised of one or more doors and, in the embodiment shown, there are two doors that have their outer edges pivotally affixed to the end walls and the inner edges of the doors come together in a slight overlapping relationship when the doors are in their closed, latched positions. The doors are thus pivotable about vertical axes between the closed position enclosing the infant compartment and an open position where the caregiver has access to the infant compartment.

Each door has a door latch assembly that is affixed to the door at or proximate to the inner edge thereof and the door latch assembly has a movable latch member that moves vertically to extend and retract a pawl with respect to the door. The door latch assembly also includes a hook shaped member having a receptacle that faces toward the hood as the door is closed.

There is a floating catch housing affixed to the hood and which is mounted so as to have a vertical movement with respect to the hood. There are latch openings in the floating catch housing that receive the pawls of the door latch assembly on both doors such that when the pawl is moved into the latch opening of the floating catch housing to a latched position in the floating catch housing, the door is in its closed, latched position. The movable latch members are biased toward their latched positions. The floating catch housing also has a pair of pins the extend laterally outwardly from the floating catch housing.

The vertical movement of the floating catch housing allows the latching mechanism to function properly despite some warpage of the door and/or hood since there is an alignment means that moves the floating catch housing into the proper orientation with respect to the door latch assemblies. That alignment means engages the floating catch housing as the door is moved to its closed position and elevates the floating catch housing vertically until the pins are aligned with the receptacles in the hook shaped members. Further closing of the door causes the pins to enter into the receptacles and to nest therein. When so nested, there is automatically established a alignment between the floating catch housing and the door latch assembly such that the movable latch member can have its pawl enter the latch opening in the floating catch housing to positively secure the door latched to the hood.

Accordingly, with the present door latching mechanism, the floating catch housing on the hood can move vertically in order to account for warpage of the hood and/or door and yet be oriented in a fixed position when that vertical movement has established an orientation between the floating catch housing and the door latch assembly such that the movable latch member will enter the latch opening in the floating catch housing at a fixed distance and provide a secure latching. As such, by the use of the pins entering and nesting within the receptacles of the hook shaped members, the orientation of the movable latch member and the latch openings in the floating catch housing are fixed such that the movable latch member will be assured of entering the latch opening sufficiently to securely latch the door to the hood.

These and other features and advantages of the present invention will become more readily apparent during the following detailed description taken in conjunction with the drawings herein.

DETAILED DESCRIPTION OF THE INVENTION

Figure 1:
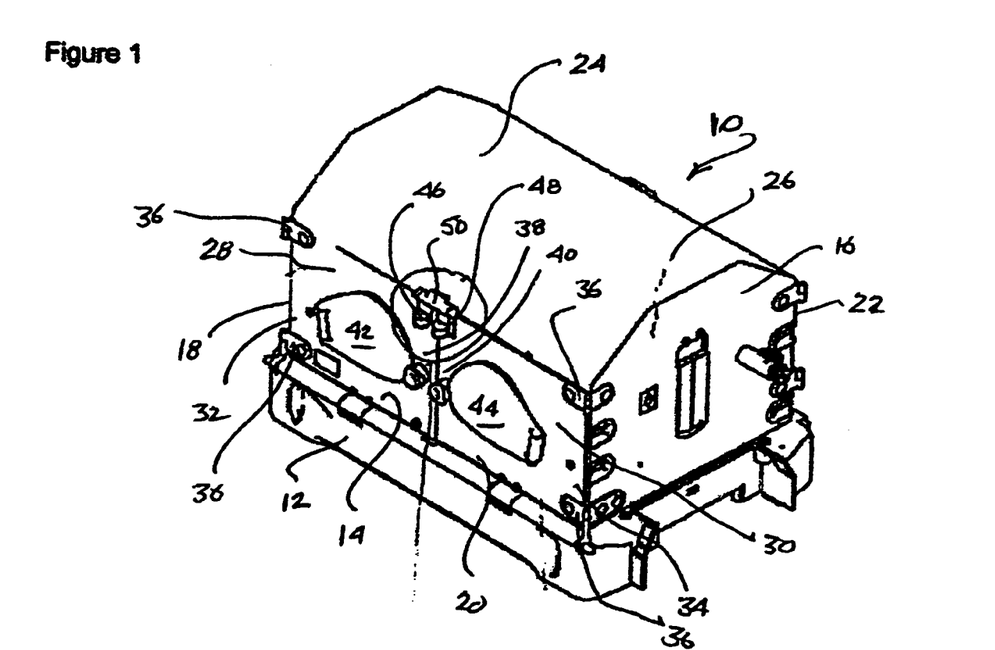
FIG. 1 is a perspective view of an infant incubator having the latching mechanism constructed in accordance with the present invention.

Referring now to FIG. 1, there is shown a perspective view of an infant care apparatus 10 constructed in accordance with the present invention.

As shown, the infant care apparatus 10 includes a base 12 that provides an infant support 14 that underlies and supports an infant. As is also seen, the infant care apparatus 10 includes a plurality of end walls 16, 18 and side walls 20, 22 and a hood 24 is located atop of the end walls 16, 18 and side walls 20, 22 in order to form an enclosed infant compartment 26 therein for containing the infant and providing a controlled environment for the well-being of the infant where the temperature within that infant compartment 26 is controlled as well as, normally, the humidity. The walls 16, 18, 20, 22 and hood 24 are preferable constructed of transparent plastic material which, however, is subject to warpage upon the presence of differential humidity conditions across the plastic material.

The heated air can be generated and circulated through the infant compartment 26 by a conventional convective heating system such as is shown and described in U.S. Pat. No. 6,213,936 of Mackin et al and which also provides a control of the humidity to suit the needs of the infant and the necessary apparatus for the convective heating system, such as the heater, fan, humidity control, air ducts and the like are normally located beneath the base 12 of the infant care apparatus 10.

In the embodiment illustrated in FIG. 1, one of the side walls 20 is comprised of two doors 28, 30 that can be opened when the caregiver desires access to the infant compartment 26 to, for example, carry out some intervention on the infant contained therein, and closed to reestablish the confined environment of the infant compartment 26. The doors 28, 30 each has an outer edge 32, 34 respectively, and those outer edges 32, 34 are pivotally affixed to the end walls 16, 18 by means of hinges 36 so that the outer edges 32, 34 of the doors 28, 30 are pivotally affixed to the end walls 16, 18 and thus with respect to the base 12 along vertical axes. In the illustrated embodiment, two side by side doors 28, 30 are shown and will be described herein, however, it can readily be seen that there can be only a single door provided as a side wall of the infant care apparatus and that single door may be pivotally affixed with respect to the base 12 along a vertical or horizontal axis. As another alternative, the one or two doors may be provided in one of the end walls 16, 18 instead of one or more of the side walls 20, 22.

As also can be seen the doors 28, 30 have inner edges 38, 40 that meet at the center of the side wall 20 and may overlap slightly in order to maintain the controlled environment within the infant compartment 26. The doors 28, 30 may also have conventional handholes 42, 44 in order to provide a more limited access to the infant with less disturbance to the controlled environment of the infant compartment 26 as opposed to fully opening one of the doors 28, 30.

At or proximate to the inner edges 38, 40 of each of the doors 28, 30 there is affixed a door latch assembly 46, 48 that is used in carrying out the latching of the doors 28, 30 to the hood 24 as will be later explained. Each of the door latch assemblies 46, 48 cooperates with a floating catch assembly 50 that is affixed to the hood 24 and will also be later explained, it being sufficient at this point to note that each of the doors 28, 30 can be individually latched and unlatched from the floating catch assembly 50, and thus from the hood 24 so that either door can be opened and closed as desired by the caregiver in accessing the infant compartment 26. The order of opening depends upon the overlap at the inner edges 38, 40.

Figure 2:
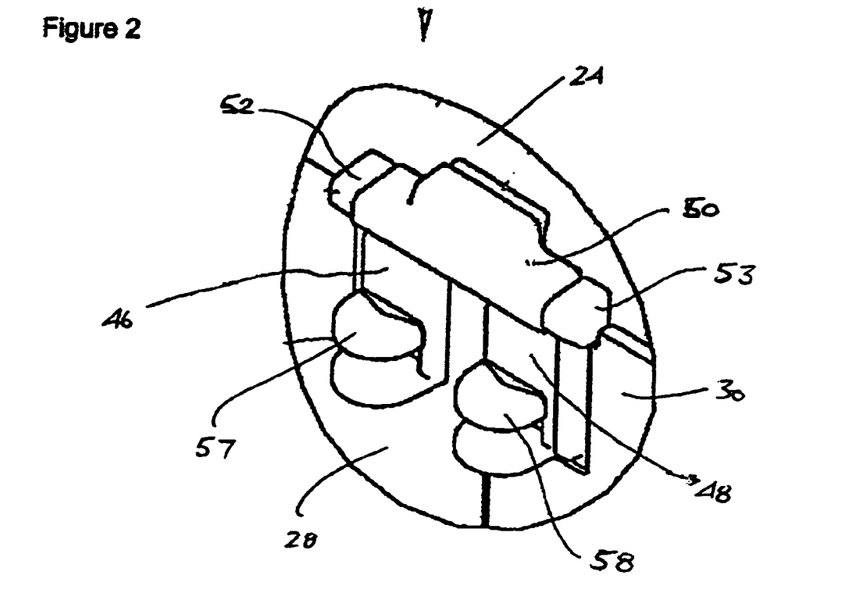
FIG. 2 is an enlarged perspective view of the latching mechanism of FIG. 1.

Turning now to FIG. 2, there is shown an enlarged perspective view of the door latch assemblies 46, 48 and the floating catch assembly 50. As shown, the floating catch assembly 50 is affixed to the hood 24 while the door latch assemblies 46, 48 are affixed to the doors 28, 30 and each of the doors 28, 30 is illustrated in the closed position abutting against the lower edge of the hood 24. Each of the door latch assemblies 46, 48 has a hook shaped member 52, 53 extending upwardly therefrom and a movable latch member 57, 58, the purpose of which will be later explained.

Figure 3:
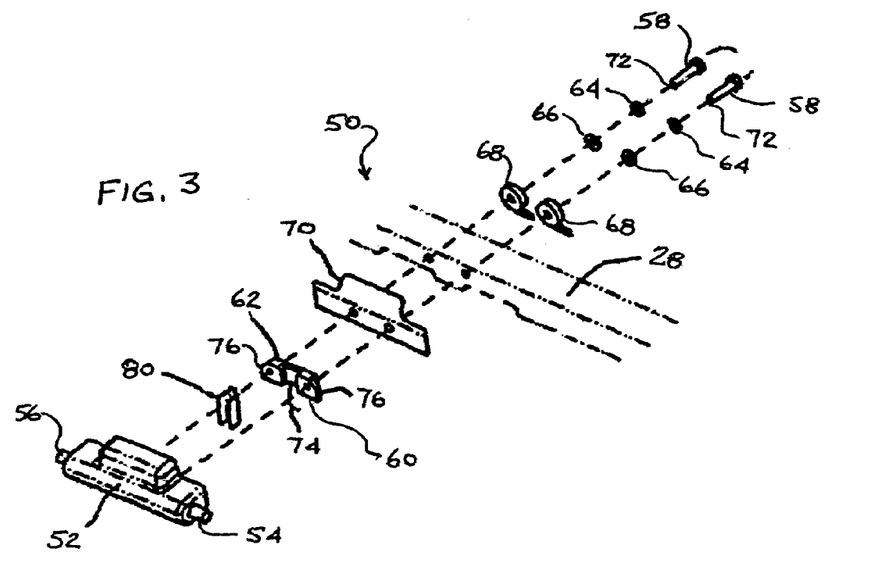
FIG. 3 is an exploded view of the floating latch component of the present latching mechanism.

Turning now to FIG. 3, there is shown an exploded view of the floating catch assembly 50 in order to illustrate its components and the affixation of the floating catch assembly 50 to the hood 24. As can be seen in FIG. 3, the floating catch assembly 50 comprises a catch housing 52 having a pair of pins 54, 56 extending laterally outwardly therefrom. The catch housing 52 is affixed to the hood 24 in a manner such that the catch housing 52 can slide vertically with respect to the hood 24 by a special fastening means. Thus, there are screws 58 that pass through the lower edge of the hood 24 and are threadedly engaged into threaded holes 60 formed in a guide bock 62. The screws 58 also preferably pass through lock washers 64, flat washers 66 and screw covers 68 that serve the purpose of hiding some of the components of the floating catch assembly 50 to improve the overall appearance thereof. Also serving to cover up the guide block 62 is a label 70.

Accordingly, as can now be seen, the guide block 62 is tightly secured to the hood 24 by means of the screws 58 passing though the threaded holes 60 in assembling the floating catch assembly 50 to the hood 24. As will be seen, the distal ends 72 of the screws 58 pass through and extend beyond the threaded holes 60 to serve a purpose that will be later explained. The guide block 62 also features a central vertical indentation 74 and has two oppositely extending male tracks 76.

Figure 4:
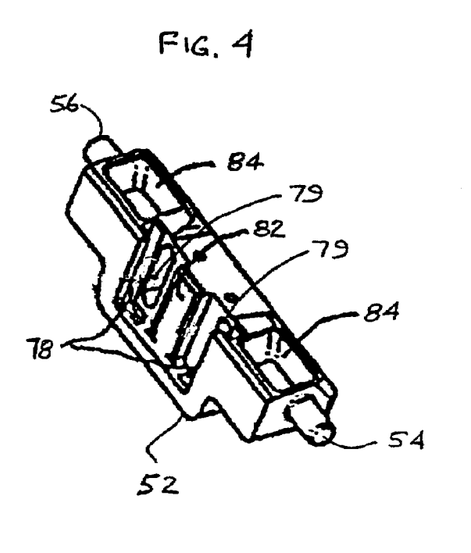
FIG. 4 is a perspective view of the latch housing of the floating latch of FIG. 3 taken for the bottom of the latch housing.

Turning now to FIG. 4 taken along with FIG. 3, there is shown a perspective view of the underside of the catch housing 52 in order to illustrate the affixation of the catch housing 52 to the hood 24 through the use of the guide block 62. As can be seen, using FIG. 4, there are female tracks 78 formed in the side of the catch housing 52 that faces the guide block 62 and the male tracks 76 of the guide block 62 enter into the female tracks 78 such that the catch housing 52 is affixed to the guide block 62 and can slide vertically therein. The extent or limits of that vertical motion is controlled to have an upper and a lower limit of motion by means of the vertical elongated pockets 79 also formed in the catch housing 52. As previously stated, the distal ends 72 of the screws 58 pass entirely through and extend beyond the threaded holes 60 and enter the vertical elongated pockets 79 formed in the catch housing 52.

As such, therefore, the upper and lower limit of the vertical movement of the catch housing 52 is determined by the distal ends 72 of the screws 58 moving within the vertical elongated pockets 79. Thus, as now can be seen, the catch housing 52 can freely move vertically with respect to the hood 24 and its downward movement is by means of gravity, however, there is a damping device 80 that damps the movement of the catch housing 52 in the downward direction.

The damping device 80 is an elastomeric material and, in the illustrated embodiment, the damping device 80 is a flat elastomeric sheet that is folded and placed in the damping recess 82 of the catch housing. In position, the fold of the damping device 80 bears on the vertical indentation 74 of the guide bock 62 to provide a small but constant friction over the whole range of travel of the catch housing 52 relative to the guide block 62. The vertical indentation 74 deforms the elastomer in a wave so that the deformation energy and friction is constant over that range of travel. The use of the damping device 80 prevents the catch housing 52 from falling downwardly in an unrestricted manner and which could startle the infant when the catch housing 52 reaches its lowermost point of travel.

As can be further seen, there are a pair of latch openings 84 formed in the lower surface of the catch housing 52 and the purpose and function of the latch openings 84 will also be later explained.

Figure 5:
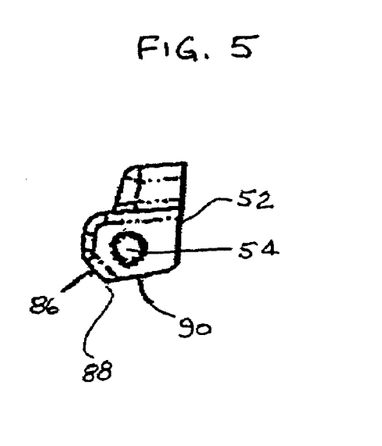
FIG. 5 is a side view of the latch housing of FIG. 3.

Turning briefly to FIG. 5, there is shown a side view of the catch housing 52 and illustrating the lower surface thereof. As seen, there is an initial downwardly sloped lead chamfer 86 reaching a lowermost point 88 whereupon the lower surface then slopes upwardly with a trailing ramp 90.

Figure 6:
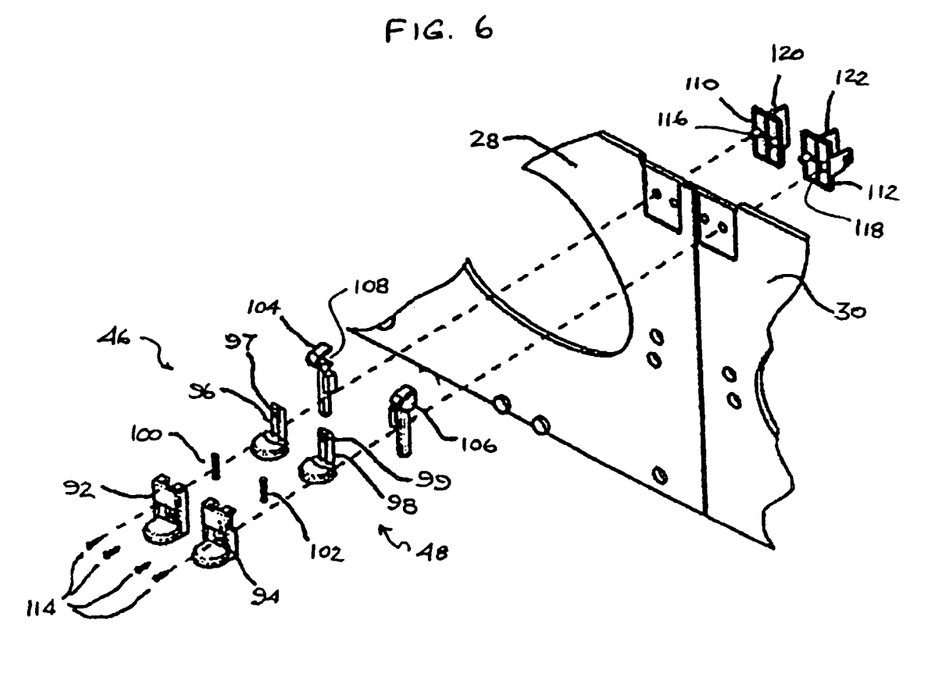
FIG. 6 is an exploded view of the door latch assembly of the present invention.

Turning next to FIG. 6, there is an exploded view illustrating the affixation of the door latch assemblies 46, 48 to the doors 28, 30 respectively. As can be seen, each door latch assembly 46, 48 comprises a latch cover 92, 94 that is affixed to the doors 28, 30 respectively, and therefore fixed in position to the doors 28, 30. Each latch cover 92, 94 also has a corresponding movable latch member 96, 98 that is vertically movable with respect to the fixed latch covers 92, 94 between a upper, latched position and a lower unlatched position. At the tip of the each of the movable latch members 96, 98 there is a latch pawl 97, 99, respectively, and which has a brightly colored warning indicator marked thereon to serve a purpose that will be later described. Springs 100, 102 are located intermediate the movable latch members 96, 98 and the fixed latch covers 92, 94 provide a bias to the movable latch members 96, 98 biasing those latch members 96, 98 toward their latched positions.

There are also hook shaped members 104, 106 that are affixed to the outer sides of the latch covers 92, 94 and each hook shaped member 104, 106 has a receptacle 108 formed in the side facing the doors 28, 30. In FIG. 6, only one of the receptacles 108 is shown, it being understood that a similar receptacle is formed in the hook shaped member 106. A pair of inner latch covers 110, 112 are located on the inside surface of the doors 28, 30 and screws 114 pass through the latch covers 92, 94 and into threaded bosses 116, 118 on the inner latch covers 110, 112 in order to join the latch covers 92, 94 to the inner latch covers 110, 112 sandwiching the doors 28, 30 therebetween.

The inner latch covers 110, 112 each have an upper alignment surfaces 120,122 that slope downwardly in the direction away from the doors 28, 30 As will be seen, the upper alignment surfaces 120, 122 form a part of an alignment means that is used to assure the proper orientation of the door latch assemblies 46, 48 to the catch housing 52 when the doors 28, 30 are moved into their closed, latched positions.

Turning now to FIGS. 7A-7D, the are shown cross sectional, schematic views of the door latching mechanism of the present invention to illustrate the sequential closing of a door 28, it being obvious that both doors close and open in the same manner. The cutaway is through the hook shaped member 106.

Figures 7A, 7B, 7C, 7D:
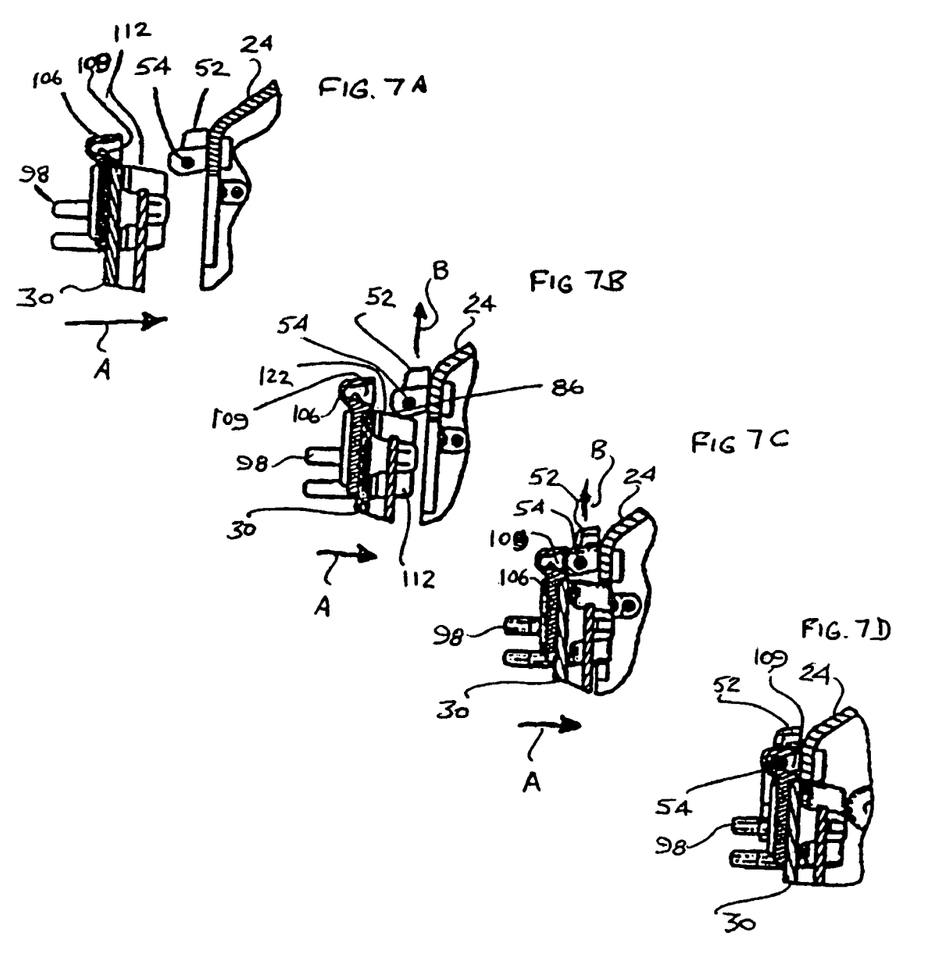
FIGS. 7A-7D are side cross sectional schematic views illustrating the sequence of closing a door to a hood utilizing the present invention.

Taking, therefore, FIG. 7A first, the door 30 can be seen to be approaching the hood 24 in the direction of the arrow A, but there has not yet been any engagement between the door latch assembly 48 and the catch housing 52. In FIG. 7B, the door latch assembly 48 has engaged the lead chamfer 86 of the catch housing 52 and the catch housing 52 is moving vertically upwardly in the direction of the arrow B along the upper alignment surface 122 of the inner latch cover 112. As thus can be seen, in the event there has been any warpage of the hood 24 in the vertical direction, the alignment means will capture the catch housing 52 and lead it into the proper orientation with respect to the door latch assembly 48 to assure a positive latching of the door 30 in its closed position.

Thus in FIG. 7C, the catch housing 52 has continued to be elevated vertically, along arrow B, until the pin 54 is aligned with the receptacle 109 in the hook shaped member 106. Finally in FIG. 5D, the door 30 has continued to be moved toward its closed position such that the pin 54 has entered into and now nests within the receptacle 109 in the hook shaped member 106, thereby assuring that the door latch assembly 48 is properly oriented both horizontal and vertically with the catch housing 52 to, again, assure that the movable latch member 98 (FIG. 6) has securely entered into and thus engaged the latch opening 84 (FIG. 4).

At the point shown in FIG. 7D, the movable latch member 98 has entered into the latch opening 84 (FIG. 4) and since the pin 54 has been nested in the receptacle 109, the vertical distance between the door latch assembly 48 and the catch housing 52 is fixed and the movable latch member 98 can enter into the latch opening 84 to the extent necessary to securely latch the door 30 to the hood 24.

Figure 8:
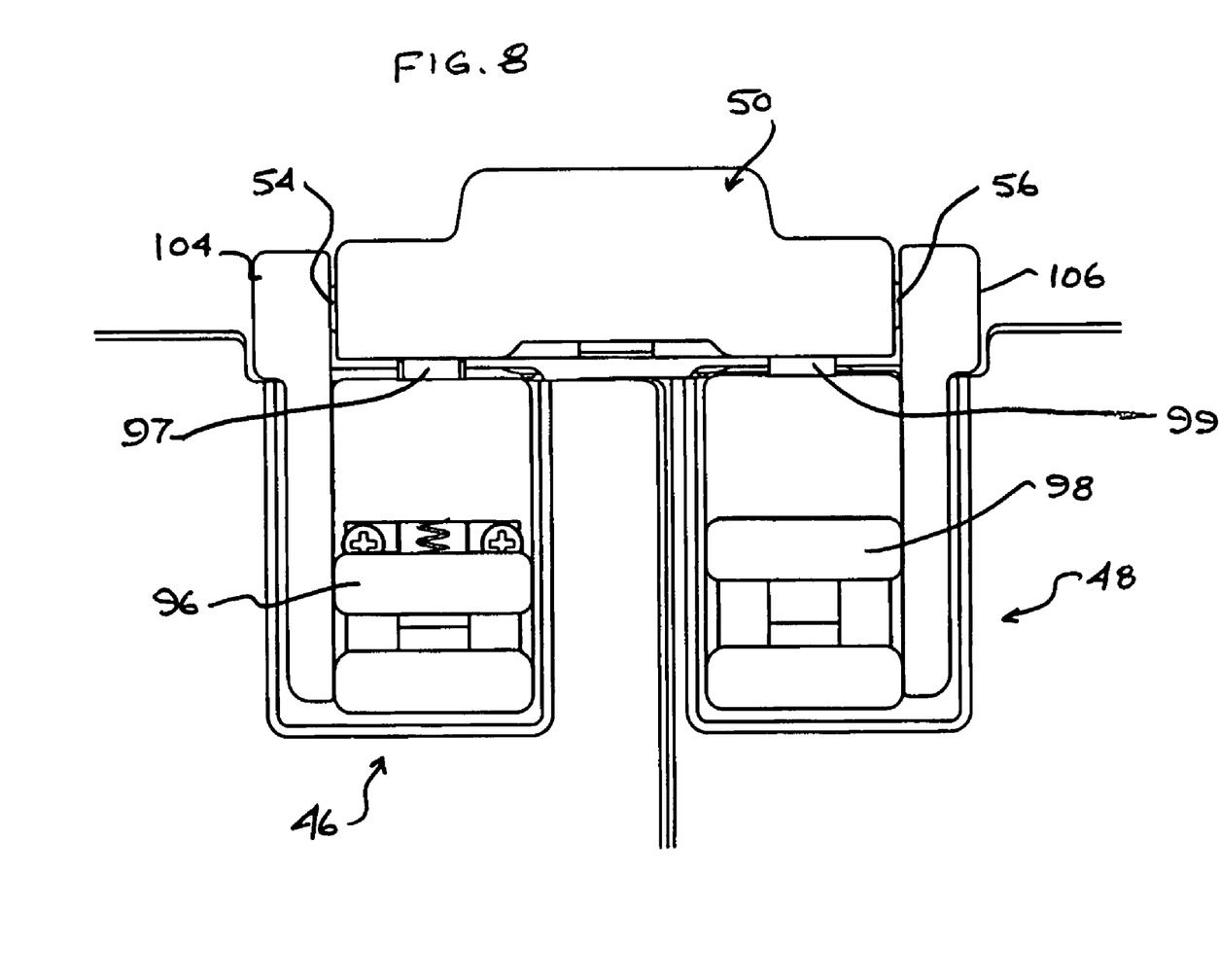
FIG. 8 is front view of the latching mechanism showing one door latch assembly in the latched position and another hood latch assembly in the partially unlatched position.

Turning finally to FIG. 8, there is shown a front view of the present door latching mechanism illustrating one door latch assembly 46 in the partially unlatched position and the other door latch assembly 48 in its latched position. As can therefore be seen, the movable latch member 96 is in a lowered position and the movable latch member 98 is in its upper, latched position. The pins 54, 56 have both been nested within the receptacles formed in the hook shaped members 104, 106 so that the vertical distance between the latch housing 52 and the door latch assemblies 46, 48 is a fixed distance. That fixed vertical distance ensures, for example, that when the movable latch member 96 is in its lower, partially unlatched position, the latch pawl 97 will not extend into the latch opening 84 (FIG. 4) and since the tip of the latch pawl 97 is a bright color, such as orange, the latch pawl 97 is visible to the caregiver to indicate that the latch pawl 97 is not engaged sufficiently into the latch opening 84 (FIG. 4).

On the other hand, the movable latch member 98 is in its upper, latched position such that the orange coloring of the latch pawl 99 is hidden from view by catch housing 52. With that lack of the orange color showing, the caregiver can be assured that the door latch assembly 48 is fully in its latched position and the door 30 is securely latched to the hood 24.

Those skilled in the art will readily recognize numerous adaptations and modifications which can be made to the latching mechanism for an infant care apparatus of the present invention which will result in an improved mechanism, yet all of which will fall within the scope and spirit of the present invention as defined in the following claims. Accordingly, the invention is to be limited only by the following claims and their equivalents.

What is claimed is:

1. An infant care apparatus, said apparatus comprising a base having an infant support on which an infant is adapted to be positioned, said apparatus having side and end walls extending upwardly from the base and a hood atop of the walls to form an infant compartment, at least one door forming one of said side or end walls, the at least one door having an outer edge pivotally mounted with respect to the base to allow the at least one door to move between a closed position enclosing the infant compartment and an open position providing access to the infant compartment, a latching mechanism to secure the at least one door in the closed position, said latching mechanism comprising a catch housing vertically movably affixed to the hood and having a pin extending therefrom and a latch opening, a door latch assembly affixed to the at least one door, said door latch assembly having a receptacle and a movable latch member, said latching mechanism having an alignment means to move the catch housing, including the pin, vertically with respect to the hood to align the pin with the receptacle to allow said pin to enter and nest within said receptacle, wherein the nesting of the pin within the receptacle orients the latch opening of the catch housing with the movable latch member to allow the movable latch member to enter the latch opening of the catch housing when said at least one door is moved to said closed position.

2. The infant care apparatus as defined in claim 1 wherein the at least one door comprises two doors each having a latching mechanism and having outer edges affixed with respect to the base to pivot about a vertical axis and said doors having inner edges and having a door latch assembly proximate to the inner edges of each of the doors.

3. The infant care apparatus as defined in claim 2 wherein a pair of pins extend outwardly from the catch housing in opposite directions wherein one of said pins is nested within one of the receptacles of the latch assemblies of the two doors.

4. The infant care apparatus as defined in claim 1 wherein the movable latch member is biased toward its latched position.

5. The infant care apparatus as defined in claim 1 wherein the alignment means comprises a sloping surface on the door latch assembly extending inwardly and downwardly in the direction toward the infant compartment and the catch housing has a lower surface wherein said sloping surface engages the lower surface of the catch housing to move the catch housing upwardly vertically as said door is moved to its closed position.

6. The infant care apparatus as defined in claim 5 wherein the lower surface of the catch housing is angled to ride up onto the sloping surface on the door latch assembly.

7. The infant care apparatus as defined in claim 1 further including a damper to damp the movement of the catch housing in the downward direction.

8. The infant care apparatus as defined in claim 7 wherein said damper comprises an elastomeric member located in between the catch housing and the hood.

9. The infant care apparatus as defined in claim 8 wherein the elastomeric member is a flat elastomeric sheet and the movement of the catch housing deforms the elastomeric sheet in a wave that provides a constant deformation energy and friction over the movement of the catch housing.

10. A latching mechanism to latch a door to a frame having a hood atop of the frame to form an infant compartment, the door having an outer edge pivotally mounted with respect to the frame to allow the door to move between a closed position abutting against the frame and an open position displaced away from the frame, a latching mechanism to secure the door in the closed position, said latching mechanism comprising a catch housing vertically movably affixed to the frame and having a pin extending therefrom and a latch opening, a door latch assembly affixed to the door, said door latch assembly having a receptacle formed therein and a movable latch member, and said latching mechanism having an alignment means to move the catch housing, including the pin, vertically with respect to the hood to align the pin with the receptacle to allow said pin to enter said receptacle to orient the latch opening in the catch housing with the movable latch member wherein the movable latch member enters into the latch opening to a latched position when said door is moved to said closed position.

11. The latching mechanism as defined in claim 10 wherein the movable latch member is biased toward its latched position.

12. The latching mechanism as defined in claim 10 wherein the alignment means comprises a sloping surface on the door latch assembly extending inwardly and downwardly in the direction toward the frame and the catch housing has a lower surface wherein said sloping surface engages the lower surface of the catch housing to move the catch housing upwardly vertically as said door is moved to its closed position.

13. The latching mechanism as defined in claim 12 wherein the lower surface of the catch housing is angled to ride up onto the sloping surface on the door latch assembly.

14. A method of latching at least one door having an outer edge pivotally affixed to an infant care apparatus having a hood and said at least one door having an inner edge so as to be movable between an open position and a closed position where the at least one door is latched to the hood forming an enclosed infant compartment within the infant care apparatus, said method comprising the steps of:

providing a catch housing having a pin extending therefrom and a latch opening, mounting the catch housing to the hood to be vertically movable with respect to the hood, providing a door latch assembly having a receptacle formed therein and an alignment means, mounting the door latch assembly proximate to the inner edge of the at least one door, moving the at least one door to its closed position wherein the alignment means moves the catch housing vertically to align the pin with the receptacle to enable the pin to enter and nest within the within the receptacle, wherein that alignment orients the latch opening in the catch housing with the movable catch member to allow the movable latch member to enter into the latch opening to a latched position securely latching the door to the hood.

15. The method of latching at least one door to a hood as defined in claim 14 wherein the step of providing a door latch assembly comprises providing a door latch assembly having an alignment means that comprises a sloping surface that extends outwardly from the door latch assembly toward the infant compartment and wherein moving the door to its closed position causes the latch housing to ride upwardly vertically along the sloping surface to align the pin with the receptacle.

16. The method of latching at least one door to a hood as defined in claim 14 wherein the step of mounting the catch housing to the hood to move vertically comprises mounting the catch housing with a damper to damp the movement of the catch housing in the downward direction.

17. The method of latching at least one door to a hood as defined in claim 16 wherein the step of mounting the catch housing comprises mounting the catch housing to the hood with a damper comprised of an elastomeric member located intermediate the hood and the catch housing to damp the movement of the catch housing in the downward direction.

18. The method of latching at least one door to a hood as defined in claim 14 comprises latching a pair of doors, each having an outer edge that is pivotally affixed to the infant care apparatus along a vertical axis.

19. The method of latching a door to a hood as defined in claim 18 wherein the step of providing a door latch assembly comprises providing a door latch assembly having a movable latch member that is biased toward its latched position extending into the latch opening in the catch housing.

* * * * *